United States Patent [19]
Meislin

[11] Patent Number: 5,906,617
[45] Date of Patent: May 25, 1999

[54] SURGICAL REPAIR WITH HOOK-AND-LOOP FASTENER

[76] Inventor: Robert J. Meislin, 6234 N. 47th St., Paradise Valley, Ariz. 85253

[21] Appl. No.: 08/911,223

[22] Filed: Aug. 15, 1997

[51] Int. Cl.⁶ .................................................... A61B 17/56
[52] U.S. Cl. ............................................................ 606/72
[58] Field of Search ............................... 606/151, 72–78; 623/11, 16

[56] References Cited

U.S. PATENT DOCUMENTS

| | | |
|---|---|---|
| 3,887,699 | 6/1975 | Yolles . |
| 4,131,597 | 12/1978 | Bluethgen . |
| 4,186,448 | 2/1980 | Brekke . |
| 5,380,329 | 1/1995 | Elia et al. ................................ 606/72 |
| 5,542,594 | 8/1996 | McKean et al. . |
| 5,550,172 | 8/1996 | Regula et al. . |
| 5,554,194 | 9/1996 | Sanders . |
| 5,576,418 | 11/1996 | Jurgens . |
| 5,597,579 | 1/1997 | Bezwada et al. . |
| 5,607,687 | 3/1997 | Bezwada et al. . |
| 5,627,233 | 5/1997 | Hubbell et al. . |
| 5,630,839 | 5/1997 | Corbett, III et al. . |

OTHER PUBLICATIONS

Chvapil, et al.; Medical and Surgical Applications of Collagen; International Review of Connective Tissue Research; 1973; pp. 1–6, 9–10, 29–30, 53–54; vol. 6; Academic Press; New York and London.

*Primary Examiner*—Michael Buiz
*Assistant Examiner*—Vikki Trinh
*Attorney, Agent, or Firm*—Harry M. Weiss; Jeffrey D. Moy; Harry M. Weiss & Associates, P.C.

[57] ABSTRACT

Surgical repairs of torn or ruptured tendons and ligaments are made by re-fastening the torn or ruptured tendon or ligament with a biocompatible or bioabsorbable hook-and-loop fastener.

5 Claims, 2 Drawing Sheets

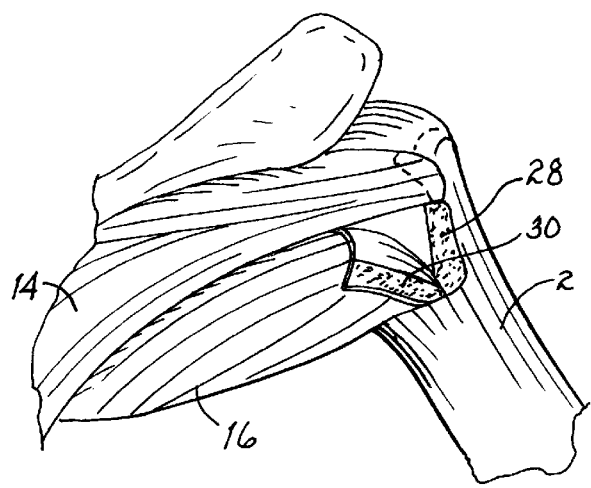
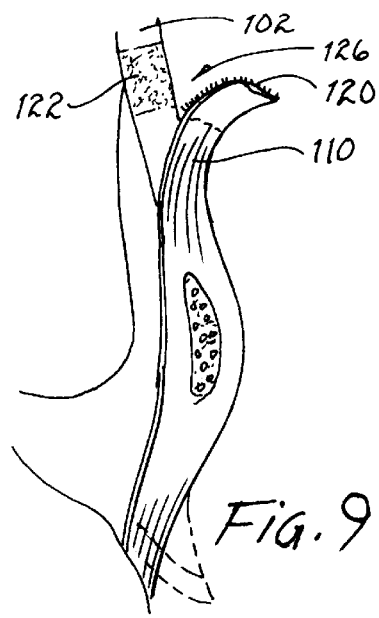
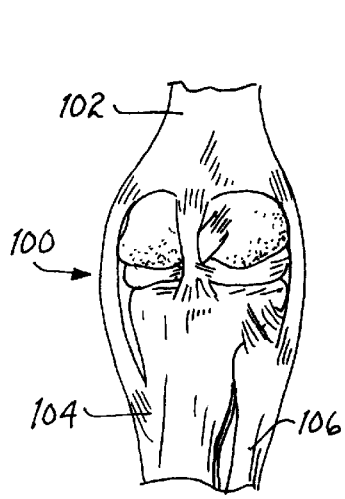
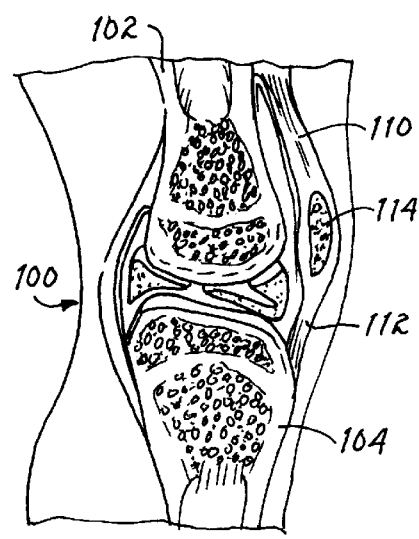
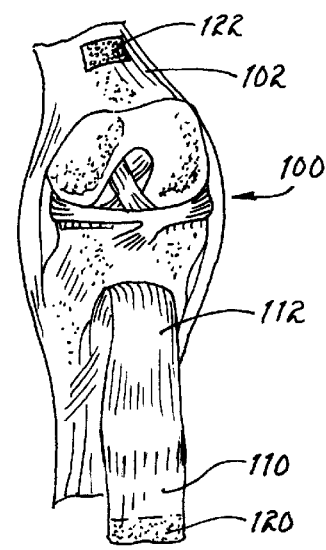
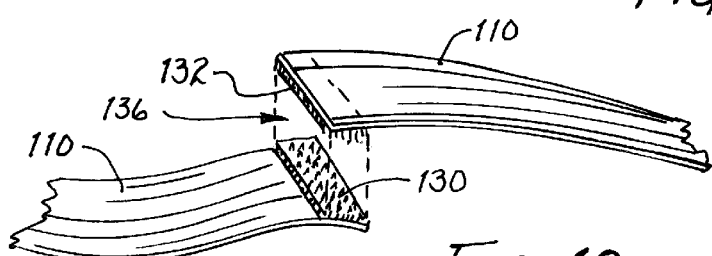

SURGICAL REPAIR WITH HOOK-AND-LOOP FASTENER

BACKGROUND OF THE INVENTION

1. Field of the Invention

This invention relates to surgical procedures generally and, more particularly, to orthopedic surgery. Specifically, this invention relates to an apparatus and method for the repair of torn or ruptured tendons or ligaments. The invention is described with respect to rotator cuff and knee ligament repairs as being examples of the application of the invention, but the invention is useful for the repair of any torn or ruptured tendon or ligament.

2. Description of the Prior Art

Human bones join with each other in a variety of ways to serve the functional requirements of the musculoskeletal system. Foremost among these needs is that of purposeful motion. The activities of the human body depend on effective interaction between normal joints and the neuromuscular units that drive them. The same elements also interact reflexively to distribute mechanical stresses among the tissues of the joint. Muscles, tendons, ligaments, cartilage, and bone all do their share to ensure smooth function. In this role, the supporting elements both unite the abutting bones and position the joints in the optimal relationship for low-friction load-bearing. Two important characteristics of normal joint function are stability and lubrication. This invention describes surgical techniques for aiding in the return of functioning to the musculoskeletal system following injuries involving for example the separation of a tendon from a bone or the rupture of a tendon or ligament due to accident or injury or overuse.

Rotator Cuff Example

The rotator cuff is composed of four muscles that blend together to help stabilize and move the shoulder. Loss of the integrity of the rotator cuff is a common cause of shoulder weakness. Persons with significant rotator cuff defects have difficulty raising the affected arm or rotating it out to the side. Strong rotator cuff tissue requires a major force to tear it. Weakened degenerative cuff tissue can be torn easily, even while carrying out activities of daily living.

The young healthy cuff is highly resistant to disruption or degeneration. Because of the change in cuff strength with age, full thickness cuff lesions are most unusual under the age of 40. When cuff lesions occur in the younger age group, they may be only partial thickness or they may include the avulsion of bone from the tuberosity. Disuse and scarring of the partial thickness lesion may lead to stiffness, limiting the range of elevation, cross-body adduction, and internal rotation.

With increasing age and disuse, less force is required to tear the cuff. Often, the acute symptoms from progression of the cuff defect are dismissed as "tendinitis" or "bursitis." Once these transient symptoms resolve, the shoulder becomes asymptomatic, except for a relatively imperceptible increment in weakness. It is not uncommon to encounter patients with large cuff defects and minimal symptoms. If these shoulders remain stable with the humeral head centered in the glenoid, they can demonstrate an astounding degree of function. Bilateral degenerative cuff defects are common. In one study it was found that 55 percent of patients presenting with a symptomatic cuff tear on one side also had a tear on the opposite side.

When rotator cuff tears are relatively recent and when a significant force was required to tear the tendon, the chances of regaining shoulder strength by rotator cuff repair surgery are good. Conversely, when the defect is long-standing and has occurred without a major injury, rotator cuff repair surgery may be a less preferred option. Thus, with long-standing shoulder weakness from rotator cuff defects, an attempt at strengthening the remaining muscles may be worthwhile before considering surgical repair.

Cuff failure may progress as major episodes of tendon tearing or as creeping tears involving relatively few fibers at a time with thinning of the cuff tendon. Degenerative lesions of the cuff typically start at the deep surface of the anterior insertion of the supraspinatus near the long head of the biceps brachii. Once these lesions begin, it is difficult for them to heal, because of the hostile environment, the compromised vascularity, the large loads, and the large deformations that the healing tissue must endure. Failure of one fiber or of groups of fibers places greater loads on the adjacent fibers, favoring their failure (the "zipper" phenomenon). When a tendon fiber fails, the muscle fiber to which it attaches produces retraction away from the site of disruption, increasing the gap needing to be closed. This retraction also places tension on the local vasculature leading to limitation of tendon blood flow in the area where healing is needed. Rotator cuff tendon defects are subject to the effects of synovial fluid on both their articular and bursal sides; the fluid and its enzymes may remove the fibrin clot necessary for healing of the cuff lesion. In the absence of repair, the degenerative process tends to continue through the substance of the supraspinatus tendon to produce a full thickness defect in the anterior supraspinatus tendon. This full thickness defect tends to concentrate loads at its margin, facilitating additional fiber failure with smaller loads than those which produced the initial defect.

Once a supraspinatus defect is established, it typically propagates posteriorly through the remainder of the supraspinatus, then into the infraspinatus and teres minor. Further propagation of the cuff defect crosses the bicipital groove to involve the subscapularis, starting at the top of the lesser tuberosity and extending inferiorly. As the defect extends across the bicipital groove, it may be associated with rupture of the transverse humeral ligament and destabilization of the long head tendon of the biceps.

The concavity compression mechanism is compromised by cuff disease. Beginning with the early stages of cuff fiber failure, the compression of the humeral head becomes less effective in resisting the upward pull of the deltoid. Partial thickness cuff tears cause pain on muscle contraction similar to that seen with other partial tendon injuries (such as those of the Achilles tendon or extensor carpi radialis brevis). This pain produces reflex inhibition of the muscle action. In turn, this reflex inhibition along with the absolute loss of strength from fiber detachment makes the muscle less effective in balance and stability. The weakened cuff function allows the humeral head to rise under the pull of the deltoid, squeezing the cuff between the head and the coracoacromial arch. Under these circumstances, abrasion occurs with humeroscapular motion, further contributing to cuff degeneration. Degenerative traction spurs develop in the coracoacromial ligament which is loaded by pressure from the humeral head (analogous to the calcaneal traction spur that occurs with chronic strains of the plantar fascia). Upward displacement of the head also wears on the upper glenoid lip and labrum, reducing their contributions to the effective depth of the upper glenoid and to glenohumeral stability from concavity compression. Further deterioration of the cuff allows the tendons to slide down below the center of the humeral head, producing a "boutonniere" deformity. The cuff tendons become head elevators rather than head depressors. Once the full thickness of the cuff has failed, abrasion of the humeral articular cartilage against the coracoacromial arch may lead to a secondary degenerative joint disease known as cuff tear arthropathy.

The progression from partial thickness tear toward cuff tear can take place as a subtle and even subclinical degenerative process, with a few fibers giving way at a time. It can also progress as a series of episodes interpreted as "tendinitis," "bursitis," or "impingement syndrome." A more significant injury can produce an acute extension of the defect. It is important to note that cuff defects arising with minimal or no injury suggest that the cuff tissue is of poor quality and thus is more likely to fail again after surgical repair. By contrast, acute tears resulting from major injuries are more likely to involve robust tissue that is more amenable to a durable repair.

The disuse of torn tendon leads to scarring and atrophy of tendon and muscle. Loss of cuff material from the degenerative process limits what is available for repair. Local injections of steroids may further compromise the healing potential of failed cuff fibers. Once the humeral head has started to subluxate superiorly, increased stretching loads are placed on the residual tendons, tending to exacerbate the cuff defect. Long-standing superior subluxation leads to erosion of the upper glenoid lip, favoring continued superior subluxation even after cuff repair. Once the process of superior subluxation is established, stabilization of the humeral head in its normal position is difficult even if a cuff repair is achieved. In summary, rotator cuff defects are common causes of shoulder weakness.

Usually, cuff tears are associated with degenerative changes, which make the tissue susceptible to failure with low applied loads, especially those applied eccentrically. Alternatively, cuff tears can occur in stronger cuff tissue, but these injuries require the application of much greater loads. Cuff defects produce weakness of elevation and external rotation as well as a possible loss of stability of the humerus against upward displacing loads from the deltoid. Shoulders may be comfortable and able to carry out certain functions in the presence of significant cuff defects. Rotator cuff surgery can restore the strength of the shoulder if the cuff tissue is of sufficient quantity and quality. To minimize the risk of retear, a substantial period of minimal loading needs to follow cuff repair surgery. Returning to heavy work after a cuff repair risks the integrity of the repair. Preservation of deltoid function is essential in rotator cuff surgery. If the function of both the cuff and deltoid are lost, glenohumeral arthrodesis may represent the only surgical option for salvage.

Surgical exploration and attempted cuff repair is an option for the patient who understands the limitations of this procedure. Prompt surgical exploration of the rotator cuff is considered for physiologically young patients with acute tears. Repair should be carried out before tissue loss, retraction, and atrophy occur. For tears older than 12 months, a period of stretching and gentle strengthening exercises can indicate the potential for nonoperative management. Exploration is considered for patients with functionally significant weakness from longer-standing tears refractory to nonoperative management, provided that their expectations are realistic.

The goal of cuff repair surgery is to improve the strength and muscular balance of the shoulder. This operative procedure is considered when the shoulder demonstrates weakness from a cuff defect and when there appears to be a substantial chance of improvement from such surgery, for example where a physiologically sound cuff has been torn acutely by a substantial injury. In this situation, the quality and quantity of tendon for repair should be excellent. By contrast, with chronic massive degenerative tears the quantity and quality of the cuff are less likely to be optimal for surgical repair. In this situation, the surgeon and the patient must understand preoperatively the potential limitations imposed by the tissue in the shoulder.

It must be remembered that there are several ways in which surgery may worsen the function of a cuff-deficient shoulder. These need to be reviewed before each cuff operation. The most serious is compromise of the deltoid muscle. The deltoid may be compromised by nerve injury. This injury may involve the intramuscular motor branches to the anterior third of the muscle resulting from a too-distal split of the muscle in the surgical approach. Deltoid denervation may also arise from axillary nerve injury when searching for cuff tendons laterally and posteriorly around the quadrangular space. Normally the deltoid has a strong tendon of origin between its anterior and middle thirds. This tendon attaches to the anterior lateral corner of the acromion. Postoperative function of the deltoid may be compromised by failure to achieve a strong reattachment of this tendon and the anterior muscle fibers after acromioplasty. This is particularly a problem when a large anterior acromial resection is performed requiring stretch of the deltoid for reattachment. Failure of the anterior deltoid origin devastates the most important motor for shoulder elevation.

The cuff is generally approached though an acromioplasty incision in the skin lines perpendicular to the deltoid fibers. This incision offers an excellent exposure and the opportunity for a cosmetic closure, particularly in comparison with the skin incisions parallel to the deltoid fibers. Great care is taken to preserve the tendon fibers of the deltoid. The deltoid has an important tendon of origin between its anterior and middle thirds. Arising from the anterior lateral corner of the acromion, this tendon is not only the guide to exposure of the cuff, but is also the key to reattachment of the deltoid origin at the conclusion of the surgery. This tendon is generally split longitudinally for 2 cm distal to the acromion in line with its fibers, taking care to leave some of the tendon on each side of the split. The split is continued up over the acromion and into the trapezius insertion. For 1 cm on either side of this split the deltoid origin is sharply dissected off the acromion, so the strong bony attachment fibers remain with the muscle. These fibers provide a strong "handle" on the muscle, so a solid repair can be achieved. Splitting the parietal layer of the bursa on the deep aspect of the deltoid provides a view of the rotator cuff. Before a "reflex" acromioplasty is performed, the quality and quantity of the cuff tissue are observed to determine the likelihood of cuff reparability. Hypertrophic bursa and scar tissue are resected to allow a good view of the cuff tissue.

Cuff tears have been characterized based on the number of tendons torn. The quality of the cuff tissue may be characterized in terms of its ability to hold a strong pull applied to a suture passed through its edge. Finally, it is critical to note the amount of tissue that has been lost. The extent of tissue loss and the ability of the remaining tissue to hold suture are the major determinants of cuff reparability. Cuff tears are also characterized by the size of the tear. A small tear is less than one centimeter, a moderate tear is between one and three centimeters, a large tear is between three and five centimeters, and a massive tear is greater than five centimeters.

When a massive cuff defect coexists with a detached, denervated, or dysfunctional deltoid, a glenohumeral arthrodesis provides a salvage option. By securing the humeral head to the scapula, the scapular motors can be used to power the humerus through a very limited range of humerothoracic motion. A fusion technique may preserve all remaining deltoid function.

If inspection of the cuff at surgery reveals good quality tissue in sufficient quantity for a robust repair, primary glenohumeral stability from concavity compression can usually be restored. Thus, a standard anteroinferior acromioplasty is performed to improve exposure and to protect the repair from abrasion. A flexible osteotome is directed so that the anterior undersurface of the acromion is resected in the same plane as the posterior acromion. Rough spots are smoothed with a motorized bur.

The goal of repair is a strong fixation of the tendon to the humerus under normal tension with the arm at the side. The desired attachment site is at the sulcus near the base of the tuberosity. This goal is facilitated by using three stages of sequential release. These releases are required because the cuff is usually retracted and because tissue is lost in chronic cuff disease. Unless these releases are carried out, increased tension in the repaired tendon will predispose to tightness of the glenohumeral joint and will additionally challenge the repair site. The humeral head is rotated to present the different margins of the cuff defect through the incision, rather than enlarging the exposure to show the entire lesion. The deep surface of the cuff is searched for retracted laminations. In prior art techniques, all layers of the cuff are assembled and tagged with sutures. By applying traction to these sutures, the cuff is mobilized sequentially as necessary to allow the torn tendon edge to reach the desired insertion at the base of the tuberosity. First, the humeroscapular motion interface is freed between the cuff and the deltoid, acromion, coracoacromial ligaments, coracoid, and coracoid muscles. Next, the coracohumeral ligament/rotator interval capsule is sectioned around the coracoid process to eliminate any restriction to the excursion of the cuff tendons and to minimize tension on the repair during passive movement. This release of the coracohumeral ligament and rotator interval capsule also contributes to better the surgical repair by mininizing the capsular tightening effect of cuff repair. At this point the ease with which the cuff margins can be approximated to their anatomic insertion at the base of the tuberosity is evaluated. If good tissue cannot reach the sulcus, the third release is carried out. This release divides the capsule from the glenoid just outside the glenoid labrum, allowing the capsule and tendon of the cuff to be drawn further laterally toward the desired tuberosity insertion without restricting range of motion.

The surgeon first makes a judgment concerning the site at which the cuff can be implanted into the bone without undue tension while the arm is at the side. Ideally, the site of implantation will be in the sulcus at the base of the tuberosity. In large cuff defects, a somewhat more medial insertion site may be necessary. Often, when a medial insertion site is required for a large cuff defect, the new insertion lies in an area where the articular cartilage has been damaged by abrasion against the undersurface of the acromion.

Traditionally, the repair is accomplished as a tongue in groove, with the cuff tendon drawn into a trough near the tuberosity, providing a smooth upper surface to glide beneath the acromion. This groove provides the additional advantage that if some slippage occurs in the suture fixation of the cuff to bone, contact between the tendon and bone is not lost. Nonabsorbable sutures passed through the tendon margin are then passed through drill holes in the distal tuberosity so that the knots will not catch beneath the acromion. The knots are tied over the tuberosities so that they will lie out of the subacromial space. If there is a longitudinal component to the tear, it is repaired side-to-side with the knots buried out of the humeroscapular motion interface. The repair is checked throughout a range of motion to 140 degrees of elevation and 40 degrees of external rotation to assure that it is strong, it is not under excessive tension, omial motion. If additional resection of the undersurface of the acromion is required to allow smooth passage of the repaired tendon, it is performed at this time.

Knee Tendon Repair Example

Knees are remarkable mechanisms, able to absorb three times the body's weight with every step taken. But the rigor of sports added to everyday walking can make the knees extra vulnerable to damage. Anyone can have knee problems. Women are especially susceptible because their wider pelvis tends to make them knock-kneed.

The bones of the knee, the femur and the tibia, meet to form a hinge joint. The joint is protected in front by the patella (kneecap). The joint is cushioned by articular cartilage that covers the ends of the tibia and femur, as well as the underside of the patella. The lateral meniscus and medial meniscus are pads of cartilage that further cushion the joint, acting as shock absorbers between the bones.

Ligaments help to stabilize the knee. The collateral ligaments run along the sides of the knee and limit sideways motion. The anterior cruciate ligament, or ACL, connects the tibia to the femur at the center of the knee. Its function is to limit rotation and forward motion of the tibia. A damaged ACL is replaced in a procedure known as an ACL Reconstruction. The posterior cruciate ligament, or PCL (located just behind the ACL) limits backward motion of the tibia. These components of the knee, along with the muscles of the leg, work together to manage the stress the knee receives as one walks, runs and jumps.

The cartilage covering our joint surfaces is called articular cartilage. Normally, it is a smooth, well-lubricated surface that offers less frictional resistance than that of an ice skate gliding on ice. Normal cartilage is very durable and somewhat elastic providing a shock absorber for our joints. Articular cartilage does not have a blood supply, rather it gets it oxygen and nutrients from the surrounding joint fluid. When a joint is loaded, the pressure squeezes fluid, including waste products out of the cartilage and when the pressure is relieved, the fluid seeps back in together with oxygen and nutrients. Thus, cartilage has a limited ability to repair itself.

Rupture of the quadriceps tendons is one of the more serious injuries to the knee and is most common in senior citizens. It is probably associated with decreased vasculature. This type of injury is more common following cortisone injections or associated with diabetes or chronic renal failure, hyperthyroidism, and gout.

The tear may involve either portion of trilaminar tendon or its entirety and usually the tear is initiated centrally and progresses peripherally. The tendon usually ruptures transversely at the osteotendinous junction and the rupture often extends through the vastus intermedius tendon, proximal to the rupture of the rectus femoris tendon.

The level of the rupture usually corresponds to amount of flexion at time of injury. Superficial and deep tears rarely involve the trilaminar structure at the same level. Unlike the Achilles tendon rupture, the quadriceps disruption is associated with intense pain.

The consequences of a tendon rupture in the knee may include large hemarthromis, a freely mobile patella and an impressive loss of extensor function. The patient is often unable to walk, may be unable to extend the knee and may demonstrate a palpable defect.

The quadriceps tendon usually ruptures transversely just proximal to patella. With partial tears an extensor lag usually is present.

Surgery to repair a tendon rupture is performed within 48 hours if possible. Early intervention allows end-to-end repair of the tendon. Traditionally, fibers of the rectus femoris tendon are sutured to superior pole of patella through drill holes. Because rupture nearly always takes place early through an area of degeneration reinforcement may be necessary.

One technique, known as the Scuderi method, involves making anterior longitudinal incision in midline of extremity to expose the rupture. The tendon ends are apposed by extending knee and pulling the proximal part of tendon ddon are sutured together. A triangular flap is fashioned from the anterior surface of proximal part of tendon about 2–3 mm thick, 7.5 cm long on each side, and 5 cm wide, leaving the base attached at a point about 5 cm proximal to the rupture. The triangular flap is turned down distally and it is sutured in place across rupture.

The prior art surgical procedures and materials rely upon sutures, staples, and/or anchors for attaching tissue to tissue and tissue to bone. Sutures are often very difficult to apply and sometimes surgery beyond making the repair per se is necessary to enable the surgeon to fix and tie the sutures. The result is increased trauma for the patient and due to the additional surgery and the time required to perform the operation. Suture placement is a demanding and exhausting effort for the surgeon.

Staples offer some simplification for certain fastening operations; however, stapled attachments may lack sufficient strength for many procedures and may increase the trauma of the surgery where staples are placed in bony structures.

SUMMARY OF THE INVENTION

It is an object of this invention to provide an improved surgical method for repairing a torn or ruptured tendon or ligament by attaching the tendon or ligament to a boney structure or to another tendon or ligament portion.

It is another object of this invention to provide a velcro-type fastener for use in surgical repair of a torn or ruptured tendon or ligament.

BRIEF DESCRIPTION OF THE PREFERRED EMBODIMENTS

In accordance with one embodiment of the present invention, a method for re-attaching at least one of a tendon and ligament to bone is disclosed. The method comprises the steps of: exposing an unattached portion of at least one of a tendon and ligament requiring attachment; exposing an attachment site on a bone for the unattached portion of the at least one of a tendon and ligament requiring attachment; affixing at least one of a hook component and loop component of a hook and loop fastener to the unattached portion of at least one of a tendon and ligament requiring attachment; affixing a complementary component of the hook and loop fastener to the attachment site for the unattached portion of the at least one of a tendon and ligament requiring attachment; and fastening the components of the hook and loop fastener.

In accordance with another embodiment of the present invention, a method for repairing a mid-substance tear is disclosed. The method comprises the steps of exposing a first unattached portion of at least one of a torn tendon and ligament; exposing a second unattached portion of the at least one of a torn tendon and ligament; affixing at least one of a hook component and loop component of a hook and loop fastener to the first unattached portion of the at least one of a torn tendon and ligament; affixing a complementary component of the hook and loop fastener to the second unattached portion of the at least one of a torn tendon and ligament; and fastening the components of the hook and loop fastener.

In accordance with a further embodiment of the present invention, a bioabsorbable hook-and-loop fastener is disclosed. The fastener comprises, in combination: a first component comprising hooks located on a sheet material; a second component comprising loops on a sheet material; and each of the sheet material, hooks and loops consisting essentially of a material suitable for use in tissue repair.

BRIEF DESCRIPTION OF THE DRAWINGS

FIG. 5 is a posterior view of a portion of the musculoskeletal structure of the human shoulder showing the attachment of one of the muscles of the rotator cuff to the greater tubercle of the humerus using a hook-and-loop fastener.

FIG. 6 is a posterior view of a knee showing a portion of the musculoskeletal structure thereof.

FIG. 7 is an side, cross-sectional view of a knee showing a portion of the musculoskeletal structure thereof.

FIG. 8 is an anterior view of a knee showing a portion of the musculoskeletal structure thereof, depicting a torn quadriceps tendon and the securement of hook-and-loop fastener components to the tendon or ligament and to the femur, respectively, for fastening the tendon or ligament to the femur.

FIG. 9 depicts the quadriceps tendon and the femur with a hook-and-loop fastener attached thereto for attaching the tendon to the femur.

FIG. 10 depicts the attachment of the ends of a ruptured achilles tendon using a hook-and-loop fastener.

DESCRIPTION OF THE PREFERRED EMBODIMENTS

This invention is described by way of examples, i.e., the attachment of rotator cuff muscles, quadriceps tendon and the joining of the ends of a ruptured tendon. It is to be understood, however, that the invention is not limited to these procedures or structures but, rather, is of general application in the attachment of tissue to bone or tissue to tissue. Moreover, while the examples given herein relate to the human anatomy, the invention disclosed and claimed herein may be used for tendon and ligament repair with other mammals as well.

Figure 1:
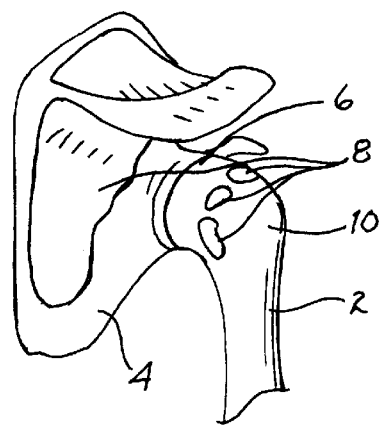
FIG. 1 is a posterior view of the skeletal bones of the human shoulder.

The first example of the use of this invention is the attachment of rotator cuff muscles and in the case of a torn rotator cuff. This example is described by reference to FIGS. 1–5, inclusive. The physiological structures of interest here are shown in the figures. The humerus 2 and the scapula 4 form a universal pivot joint between the head of the humerus 2 and the glenoid cavity 6 of the scapula 4. Referring specifically to FIG. 1, three of the muscles of the rotator cuff have posterior origins indicated generally at 8 on the greater tubercle 10 and on the scapula 4.

Figure 2:
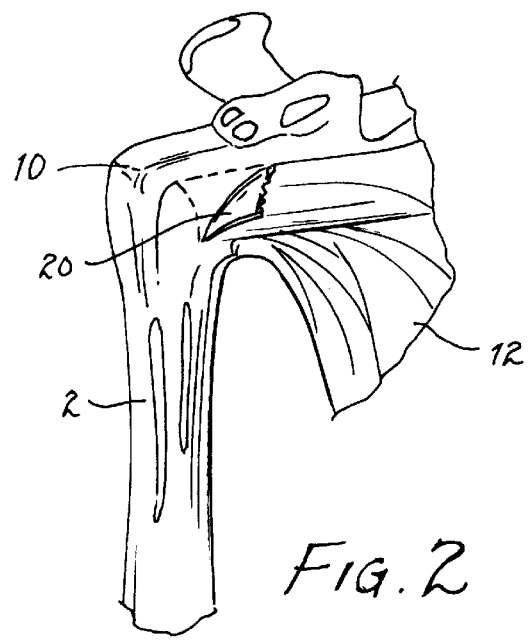
FIG. 2 is an anterior view of a portion of the musculoskeletal structure of the human shoulder showing an example of a torn rotator cuff.
Figure 3:
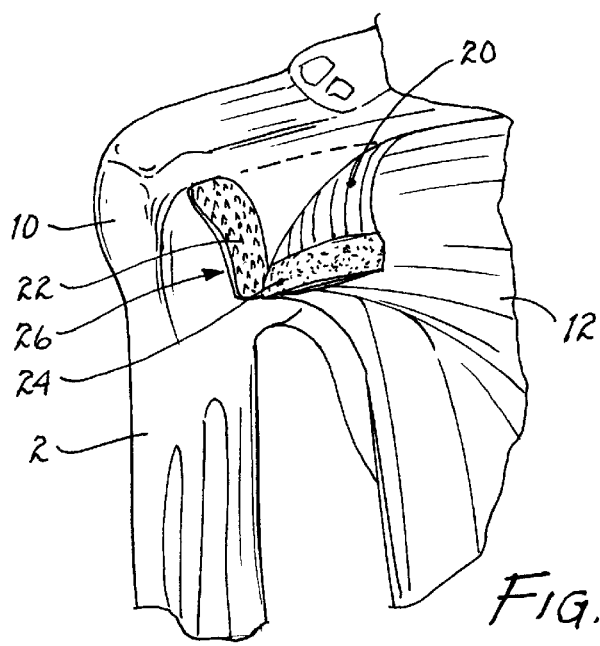
FIG. 3 is another anterior view of a lesser portion of the musculoskeletal structure of the human shoulder showing the attachment of hook-and-loop fasteners for attaching one of the muscles of the rotator cuff to the greater tubercle of the humerus.

Referring to FIG. 2, the subscapularis muscle 12 extends anteriorly between the scapula 4 and the greater tubercle 10. FIG. 2 depicts a torn subscapularis tendon 20 separated from the greater tubercle 10. FIG. 3 depicts, in enlarged view, the fixation of a hook-and-loop fastener 21 for reattaching the subscapularis tendon 20 to the greater tubercle 10, one portion of the fastener 21 being attached to each of such structures. For example, the hook portion 22 of the fastener 21 is shown fixed to the greater tubercle 10 and the loop portion 24 is shown fixed to the tendon 20.

Figure 4:
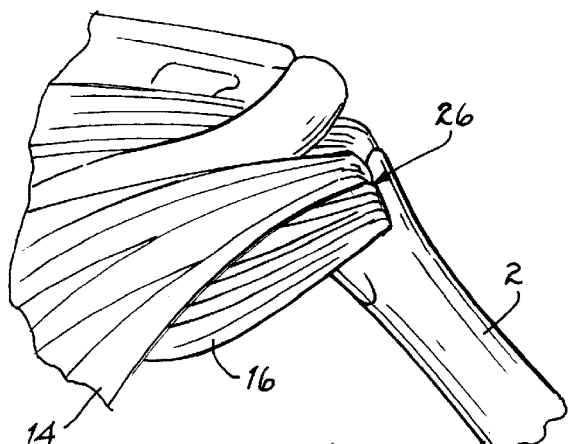
FIG. 4 is a posterior view of a portion of the musculoskeletal structure of the human shoulder showing the attachment of three of the muscles of the rotator cuff to the greater tubercle of the humerus.

Referring to FIG. 4, the attachment of two of the rotator cuff muscles, the infraspinatus muscle 14 and the teres minor muscle 16, are shown attached to the humerus 2 by a hook and loop fastener 26, the mode of attachment being depicted in more detail in FIG. 5 wherein the two components 28 and 30 of the fastener 26 are shown fixed to the teres minor muscle 16 and the humerus bone 2, respectively. Attachment may be made by means of hook-and-loop fastener 26 alone, as shown in FIG. 4, or in combination with existing suturing or anchoring techniques.

FIGS. 6 through 9 depict another exemplary application of the invention for reattaching the quadriceps tendon 110 to the femur 102. The knee joint 100, as depicted in FIGS. 6, 7 and 8, includes the ends of the femur 102 and the ends of the tibia 104 and the fibula 106. The knee joint 100 permits bending essentially in one plane. Extension of the knee results in substantial part from the contraction of muscles applying a shortening force over the anterior portion of the knee by means of the quadriceps tendon 110 and the patellar ligament 112, which attach to the kneecap or patella 114. When the quadriceps tendon 110 becomes detached from the femur 102, as shown in FIG. 8, repair requires reattachment of the quadriceps tendon 110 to the femur 102. Traditionally, as discussed above, the attachment is made with sutures and/or staples. According to this invention, the attachment is made by means of a hook-and-loop fastener 126, the two components thereof being shown at 120 and 122 in FIGS. 8 and 9. Attachment may be made by means of hook-and-loop fastener 126 alone, as shown in FIGS. 8 and 9, or in combination with existing suturing or anchoring techniques.

As discussed above, it is not uncommon for the quadriceps tendon 110 to rupture adjacent the patella 114. Referring now to FIG. 10, it is also not uncommon for other tendons or ligaments, and in particular an achilles tendon 130, to rupture—a so-called "mid-substance tear." In such cases, it is necessary to effect a satisfactory repair to join the ends of the achilles tendon 130 together. This is usually accomplished with sutures with or without additional reinforcement. According to this invention, the two ends of the achilles tendon 130 are joined together by a hook-and-loop fastener 136, alone or in combination with sutures or anchors (not shown), the two interacting portions of which fastener 136 are shown in FIG. 10 at 132 and 134.

It is emphasized that the technique of this invention may be used to attach any tendon, and some other tissues, to a bone or to another tendon or ligament or tissue.

Hook-and-loop fasteners are well-known and have found many applications but, to the knowledge of the inventor, have never been considered to be useful in tissue to bone or tissue to tissue surgical attachments. Commercially available hook-and-loop fasteners, a popular brand of which are VELCRO® fasteners, are not useful in the present invention; however, the same techniques used in manufacturing commercial hook-and-loop fasteners can be used to manufacture fasteners of this type of materials that are compatible with tissues, bones and fluids and can remain in the patient indefinitely or which are bioabsorbable and are assimilated by the body after the tissue regenerates. Further, these devices can be formed, in part, in situ, using fast drying adhesives such as fibrin glue which attach the fastener to the bone or other tissue and also attach the hooks or loops to the bone or tissue.

Many polymers are known to be biocompatible. For example DACRON® polyester is widely used as suture material and in implantable surgical devices. Polycarbonates are also generally compatible with biological tissue, etc. These and other materials can be formed into hook-and-loop fastener components using standard manufacturing methods.

Non-toxic, non-immunogenic, and bioabsorbable materials can also be manufactured or formed as hook-and-loop fasteners. Suitable materials include polylactic acid; polycaprolactone; polyglycolic acid; polyanhydrides (e.g., polyterephthalic acid/sebaic acid anhydride, polydioxanone); polyamino acids (e.g., polyglycine, etc.); and copolymers of lactic acid with comonomeric materials such as glycolic acid, hexamethyl sebacic acid, etc. These combine the best qualities of non-immunogenicity, non-toxicity and an acceptable rate of bioabsorption vs. regeneration of tissue and are preferred to prepare the surgical implant fasteners of the invention. Collagen and other polymers of biological origin (alginates, starch, etc.) are also suitable but have a potential of being immunogenic. Modified natural polymers such as gelatin, oxidized cellulose, etc., may also be utilized. Hydroxyapatite coral may also be used. Additives may be incorporated in the fastener, materials such as plasticizers, citrate esters, hexametholsebacate, antibiotics (e.g., tetracyclines, penicillins, mefronidazole, clindamycin, etc.), to prevent infection, etc., or to accomplish other desired conditions or results.

Other biocompatible and bioabsorbable materials are described, along with methods of manufacture and handling, in the following patents and publications, the disclosures of which are incorporated herein.

U.S. Pat. No. 5,627,233 issued in May 1997 to Chowdhury, et. al.

U.S. Pat. No. 5,630,839 issued in May 1997 to Clary, et. al.

U.S. Pat. No. 4,131,597 issued in December 1978 to Bluethgen, et. al.

U.S. Pat. No. 5,607,687 issued in March 1997 to Bezwada, et. al.

U.S. Pat. No. 5,597,579 issued in January 1997 to Bezwada, et. al.

U.S. Pat. No. 5,576,418 issued in November 1996 to Jurgens.

U.S. Pat. No. 5,554,194 issued in September 1996 to Sanders.

U.S. Pat. No. 5,550,172 issued in August 1996 to Bregen, et. al.

U.S. Pat. No. 5,542,594 issued in August 1996 to Hain, et. al.

U.S. Pat. No. 4,186,448 issued in February 1980 to Brekke

U.S. Pat. No. 3,887,699 issued in June 1975 to Yolles

Chavpil M. et al, "Medical and Surgical Appliances of Collagen" from *International Review of Connective Tissue Research,* vol. 6 1973 pp. 1–6, 9–10, 29–30 and 53–54.

The hook-and-loop fasteners may be fixed to the bone or tendon or ligament using fibrin glue alone or in association with sutures and/or staples. Even in those instances where suturing or stapling is required, the use of this invention permits operative techniques that are less intrusive and less traumatic. Sutures or staples may be used only for temporarily securing the fastener components while the fibrin or other biocompatible adhesive sets. In such instances, less stapling and less suturing than would be required if the entire attachment was made of sutures or staples, or a combination of the two.

Importantly, from the operative time and trauma points of view, it is easier to attach the respective components of the hook-and-loop fasteners to, e.g., the bone or to the end of a torn tendon or ligament than it is to use staples or sutures to attach the ligament to the bone or the ends of a ruptured tendon or ligament to each other.

Another important feature of this invention is that sterile hook-and-loop material may be cut at the operating table into exactly the size and shape needed to obtain the best attachment.

Additionally, sterile hook-and-loop material can be cut not only to form the attachment per se but in lengths and/or widths to provide reinforcement for weakened tissue or bone.

Still another advantage is attainable using this invention. If the tendon or ligament rupture or tear is such that the tendon or ligament is shorter than is needed to form a satisfactory attachment, the hook-and-loop material may extend beyond the end of the ruptured tendon or ligament, thus making an attachment at the proper length.

In carrying out the method of this invention, traditional surgical techniques for the particular repair may be used and the surgical procedure is the same as in traditional surgery with the exception that the attaching step comprises fixing one component of a hook-and-loop fastener to the tendon or ligament to be fastened and the other component of the hook-and-loop fastener to the bone or tendon or ligament to which the tendon or ligament is to be fastened and then attaching the two components of the hook-and-loop fastener together by pressing the hook face to the loop face of the respective components.

The invention is also embodied in a bioabsorbable hook-and-loop fastener comprising a first component comprising hooks on a sheet material and a second component comprising loops on sheet material, the sheet material, hooks and loops consisting of a material suitable for use in tissue repair.

Again, the foregoing are exemplary and the invention may be carried out using any of many materials to repair virtually any tendon or ligament tear or rupture.

What is claimed is:

1. A bioabsorbable hook-and-loop fastener comprising, in combination:

a first sheet of material;

a first component comprising hooks located on said first sheet of material;

a second sheet of material to be integrally connected to said first sheet of material;

a second component comprising loops on said second sheet of material; and each of said first sheet and said second sheet of material, said hooks and said loops consisting essentially of tissue repair material, said hooks and said loops located opposite each other to facilitate coupling of said hooks to said loops.

2. The fastener of claim 1 wherein said tissue repair material comprises a collagen-based material.

3. The fastener of claim 1 wherein said tissue repair material comprises hydroxyapetite coral.

4. The fastener of claim 1 wherein said tissue repair material comprises a non-immunogenic bioabsorbable polymer.

5. The fastener of claim 1 wherein said tissue repair material comprises a biocompatible polymer.

* * * * *